United States Patent [19]

Martin

[11] Patent Number: 4,885,939

[45] Date of Patent: Dec. 12, 1989

[54] DYNAMOMETER FOR TESTING ECCENTRIC CONTRACTIONS AND CONCENTRIC CONTRACTIONS WITH FREE-LIMB ACCELERATION

[75] Inventor: Matt Martin, Sayville, N.Y.

[73] Assignee: Lumex, Inc., Bay Shore, N.Y.

[21] Appl. No.: 146,576

[22] Filed: Jan. 21, 1988

[51] Int. Cl.$^4$ ............... A61B 5/22; A63B 21/24
[52] U.S. Cl. ............................... 73/379; 272/129
[58] Field of Search ..................... 73/379; 272/129

[56] References Cited

U.S. PATENT DOCUMENTS

| | | |
|---|---|---|
| 2,616,416 | 11/1952 | Gillmeier . |
| 2,735,422 | 2/1956 | Jones . |
| 2,784,591 | 3/1957 | Shoor . |
| 3,134,378 | 5/1964 | Harwood . |
| 3,301,553 | 1/1967 | Brakeman . |
| 3,465,592 | 9/1969 | Perrine ............... 73/379 |
| 3,580,244 | 5/1971 | Graves . |
| 3,713,438 | 1/1973 | Knutsen . |
| 3,744,480 | 7/1973 | Gause et al. . |
| 3,784,194 | 1/1974 | Perrine . |
| 3,822,599 | 7/1974 | Brentham . |
| 3,824,993 | 7/1974 | Grant . |
| 3,848,467 | 11/1974 | Flavell . |
| 3,869,121 | 3/1975 | Flavell . |
| 3,902,480 | 9/1975 | Wilson . |
| 4,235,437 | 11/1980 | Ruis et al. . |
| 4,276,887 | 7/1981 | Hofstein . |
| 4,326,707 | 4/1982 | Strecker . |
| 4,333,340 | 6/1982 | Elmeskog . |
| 4,337,050 | 6/1982 | Engalitcheff, Jr. . |
| 4,354,676 | 10/1982 | Ariel . |
| 4,402,502 | 9/1983 | Peters . |
| 4,479,647 | 10/1984 | Smith . |
| 4,492,222 | 1/1985 | Hajianpour . |
| 4,544,154 | 10/1985 | Ariel . |
| 4,549,534 | 10/1985 | Zagorski et al. . |
| 4,601,468 | 7/1986 | Bond et al. . |
| 4,628,910 | 12/1986 | Krukowski . |
| 4,691,694 | 9/1987 | Boyd et al. . |

*Primary Examiner*—Charles A. Ruehl
*Attorney, Agent, or Firm*—Davis Hoxie Faithfull & Hapgood

[57] ABSTRACT

A human performance dynamometer for testing eccentric contractions and also concentric contractions of the human muscles. The dynamometer provides for free-limb acceleration during concentric contractions, whereby the user can accelerate the input shaft of the dynamometer to the set speed without any resistance from the dynamometer. The dynamometer has two parallel shafts which are geared together and rotate in opposite directions to one another. The dynamometer has an input shaft for connection to limb engaging means. A motor is operatively connected to one of the parallel shafts through a speed reducer. Located on each shaft is an overrunning spray clutch, each of which may be disengaged from the system if eccentric contractions are desired for one or both directions of rotation of an input shaft. Each outer race of the respective overrunning clutch is connected to its respective parallel shaft. The inner race of each overrunning clutch is geared to the input shaft. A spring clutch on one of the parallel shafts is used to lock together the inner race and the outer race of one of the overrunning clutches, thereby allowing for eccentric contractions in both directions of the rotation of input shaft when the other overrunning clutch is disengaged. A motor controller is also provided for controlling the motor.

12 Claims, 4 Drawing Sheets

DYNAMOMETER FOR TESTING ECCENTRIC CONTRACTIONS AND CONCENTRIC CONTRACTIONS WITH FREE-LIMB ACCELERATION

FIELD OF THE INVENTION

This invention relates to a human performance dynamometer for testing eccentric contractions and concentric contractions of the human muscles, to the safest extent possible, while providing for free-limb acceleration during concentric contractions.

BACKGROUND OF THE INVENTION

A dynamometer that tests both concentric contractions and eccentric contractions of the muscles of a user must absorb torque in the direction in which the user's limb is exerting a force against a handle or input arm of the dynamometer (so-called concentric muscular contractions) and must also absorb torque in the direction opposite to the direction the user's limb is exerting a force against the handle or input arm (so-called eccentric muscular contractions). Eccentric contraction is also known as passive ranging because the handle or input arm of the dynamometer is driven by an external source (such as a motor) to move the user's limb through the range of motion in both directions without any assistance by the user.

Some dynamometers have tested eccentric contractions by directly attaching the limb of the user to a drive source such as an hydraulic actuator or an electric motor via a gear box. Such systems are not particularly safe because the user cannot disengage his limb from connection to the drive source in case of pain or some sort of emergency situation. Use of a clutch which allows for quick limb disengagement from the drive source adds somewhat to the safety of such dynamometers, though in the view of some, there remains an element of danger to the user in passive ranging systems, regardless of the safety features.

Examples of prior art dynamometers include isokinetic dynamometers, such as that shown in U.S. Pat. No. 3,465,592 issued September 1969 to J. Perrine. During concentric contractions, isokinetic dynamometers offer controlled speed of movement and an accomodating resistance which automatically adjusts to always equal the force applied by the user. In other words, once the user accelerates his or her limb to the desired testing speed, the user will be unable to increase the speed of rotation of the input arm.

Known dynamometers which test both concentric and eccentric contractions make it very difficult for the user to accelerate his limb quickly or smoothly to the desired testing speed during concentric contractions because the dynamometer power source, whether it be hydraulic or electro-mechanical, must match the user's limb acceleration. If the user accelerates his limb at the fastest rate possible, the dynamometer power source may not accelerate as quickly, resulting in the power source resisting the user's limb acceleration. Since the range of motion of the input arm is limited, this condition results in having the user's limb moving at the desired testing speed for a lesser period of time during concentric contractions.

Ideally, a concentric-eccentric dynamometer should allow for free-limb acceleration during concentric contractions where the user can accelerate his or her limb up to the set speed of the dynamometer without any resistance from the dynamometer. Since such dynamometers are designed to test the user's musculature at set speeds, the failure to provide free-limb acceleration results in loss of test data and greater fatigue to the user. In addition, free-limb acceleration more closely simulates actual function, such as the swinging of the arms during a walking motion. Failure to allow for free-limb acceleration therefore results in a less natural limb movement for the user.

Such an ideal dynamometer should also provide as many safety features as possible during eccentric contractions.

Isokinetic dynamometers manufactured by Cybex Division of Lumex, Inc., Ronkonkoma, N.Y., such as the dynamometer which is part of the Cybex® 340 isokinetic testing system, use overrunning clutches which permit a servo motor power source to run continuously in one direction at a desired testing speed. The user is free to move the handle or input arm in either direction with no resistance until the set testing speed is reached. Once the set speed is reached, the user performs concentric muscular contractions, which are then precisely measured. However, the present Cybex® isokinetic system dynamometers only allow for concentric contractions, and do not permit testing of eccentric contractions. These current Cybex® dynamometers jam when the motor direction is reversed to provide for eccentric contractions. When the servo motor is running in the direction designed for concentric contractions, the clutches are overrunning in opposite directions to one another on two parallel shafts. The two parallel shafts are geared to an input shaft connected to the handle or input arm of the dynamometer. If the motor direction is reversed in an effort to eccentrically load a muscle, both clutches engage, each attempting to drive the input shaft of the dynamometer in an opposite direction, resulting in zero net movement, thus jamming the dynamometer.

Although a dynamometer which tests eccentric contractions is not inherently 100% safe to the user regardless of the number of added-on safety features, there remains a need in certain situations for a dynamometer which tests both concentric and eccentric contractions in as safe a manner as possible, particularly for eccentric contractions, and also allows for free-limb acceleration u to the test speed during concentric contractions.

SUMMARY OF THE INVENTION

The present invention is for an improved human performance dynamometer. In a preferred embodiment, the dynamometer allows for three primary modes of testing: a first mode providing for concentric muscular contractions in both directions of rotation of an input shaft of the dynamometer; a second mode providing for concentric contractions in one rotational direction of the input shaft and eccentric contractions in the other; and a third mode providing for eccentric contractions in both directions of rotation of the input shaft.

In the preferred embodiment, the dynamometer has a first parallel shaft and a second parallel shaft geared together such that the two parallel shafts rotate in opposite directions to one another. A motor through a speed reducer drives one of the parallel shafts.

Supported on each shaft is an overrunning sprag clutch, each overrunning clutch having an inner race and an outer race. Two small spur gears, which are supported one on each parallel shaft, are connected to the respective inner races of the overrunning clutches.

An input shaft, connected to a limb engaging means, is geared to each small spur gear by a large spur gear fixed on the input shaft. When the user rotates the input shaft in a first rotational direction by exerting a force against the limb engaging means, the two inner races of the overrunning clutches both rotate in a second rotational direction.

For the concentric-concentric mode of operation, the outer races of the overrunning clutches are locked to their respective parallel shaft. In the preferred embodiment, this is accomplished by pins movably attached to each parallel shaft engaging in radial holes in the outer races of each overrunning clutch. The pins are placed into engagement in the radial holes by means of a plunger for each parallel shaft, each plunger having a conical end. As an actuation device pushes each plunger, the wide section of each conical end pushes each pin up into its respective radial holes.

For the concentric-eccenrric mode, one of the overrunning clutches is disengaged by dropping the pins out of engagement with the radial holes for that parallel shaft. The user exerts a force in one rotational direction against the limb engaging means until a desired range of motion position is reached. A position sensing device attached to the input shaft senses the rotational position of the input shaft and a motor controller instructs the motor to go to zero speed at an appropriate rotational position. The motor then reverses direction to the set speed, and the user engage in eccentric contractions for that direction of rotation of the input shaft.

For the eccentric-eccentric mode of operation, a spring clutch on one of the parallel shafts is used to lock together the outer race and the inner race of the overrunning clutch on that parallel shaft. This results in an eccentric contraction in the first rotational direction of the input shaft, and when the motor reverses, an eccentric contraction in the second rotational direction of the input shaft.

DETAILED DESCRIPTION OF THE INVENTION

Figure 1:
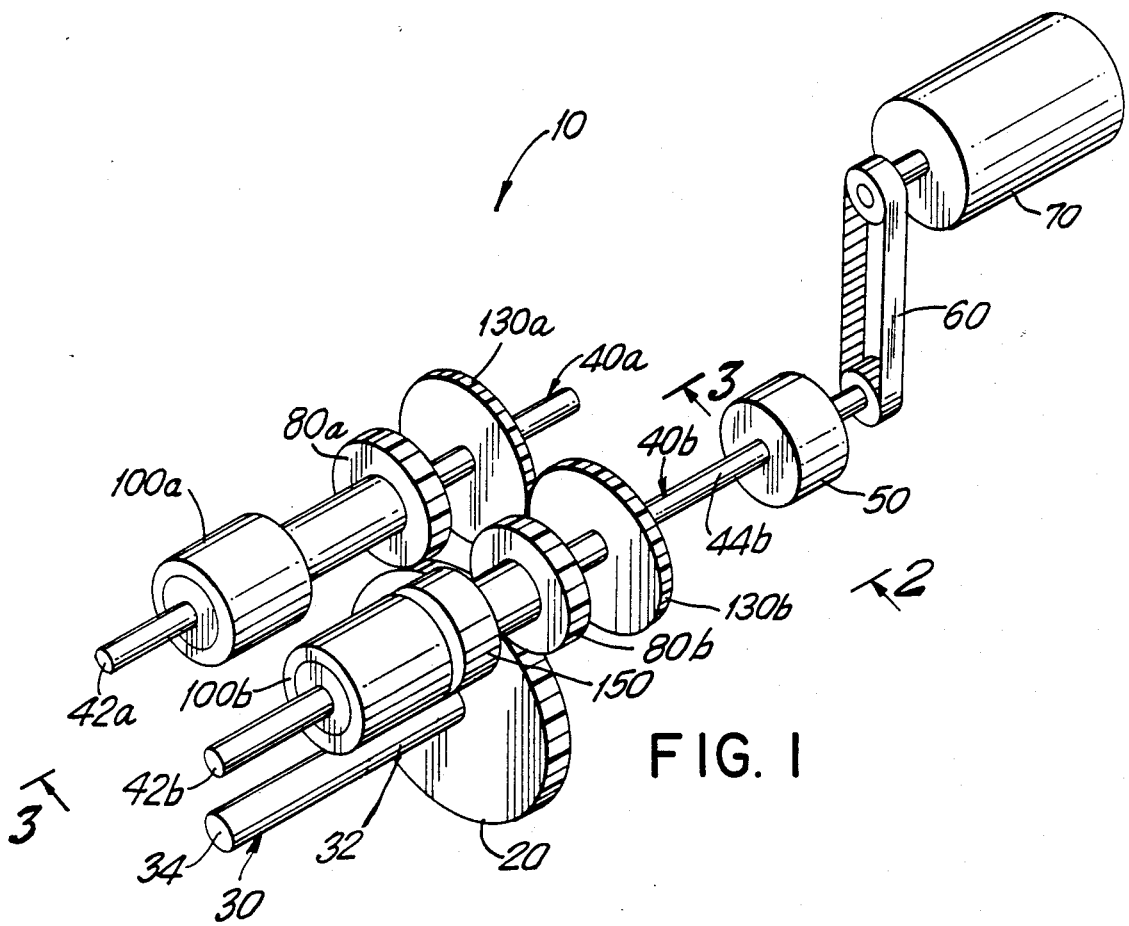
FIG. 1 is a perspective view of a dynamometer of the present invention, including a first parallel shaft, a second parallel shaft input shaft and a motor.
Figure 5:
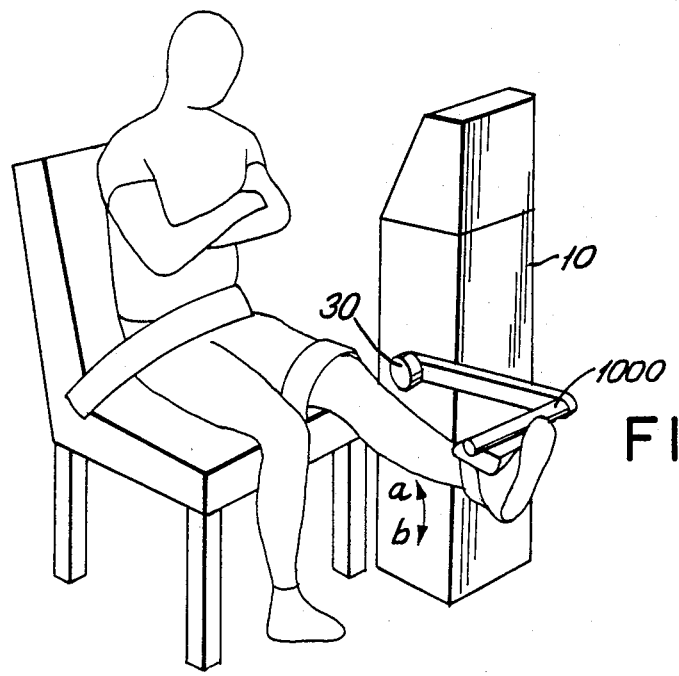
FIGS. 5–7 show exemplary uses for the dynamometer of the present invention.
Figure 6:
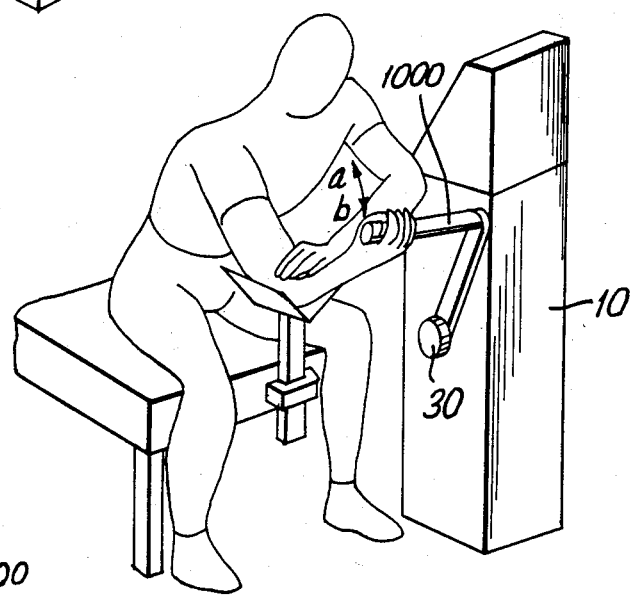
Figure 7:
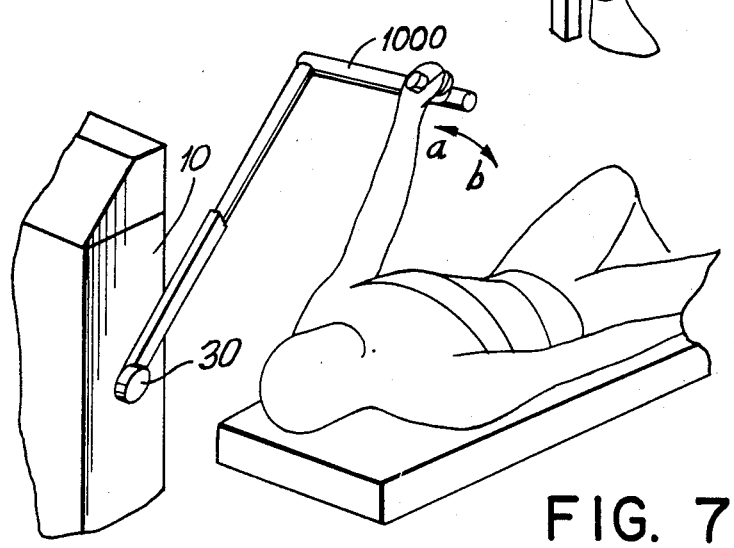

FIG. 1 shows a perspective view of a dynamometer 10 of the present invention. A large spur gear 20 is fixed by a set screw or the like to a first end 32 of an input shaft 30. A second end 34 of the input shaft 30 is connected to a handle, input arm, lever arm or the like (also known as limb engaging means 1000 as shown in FIGS. 5-7) which is used by the user's limb for rotational movement. Examples of such handles, input arms and lever arms are part of many isokinetic testing systems manufactured and sold by Cybex Division of Lumex, Inc., Ronkonkoma, N.Y.

Figure 2:
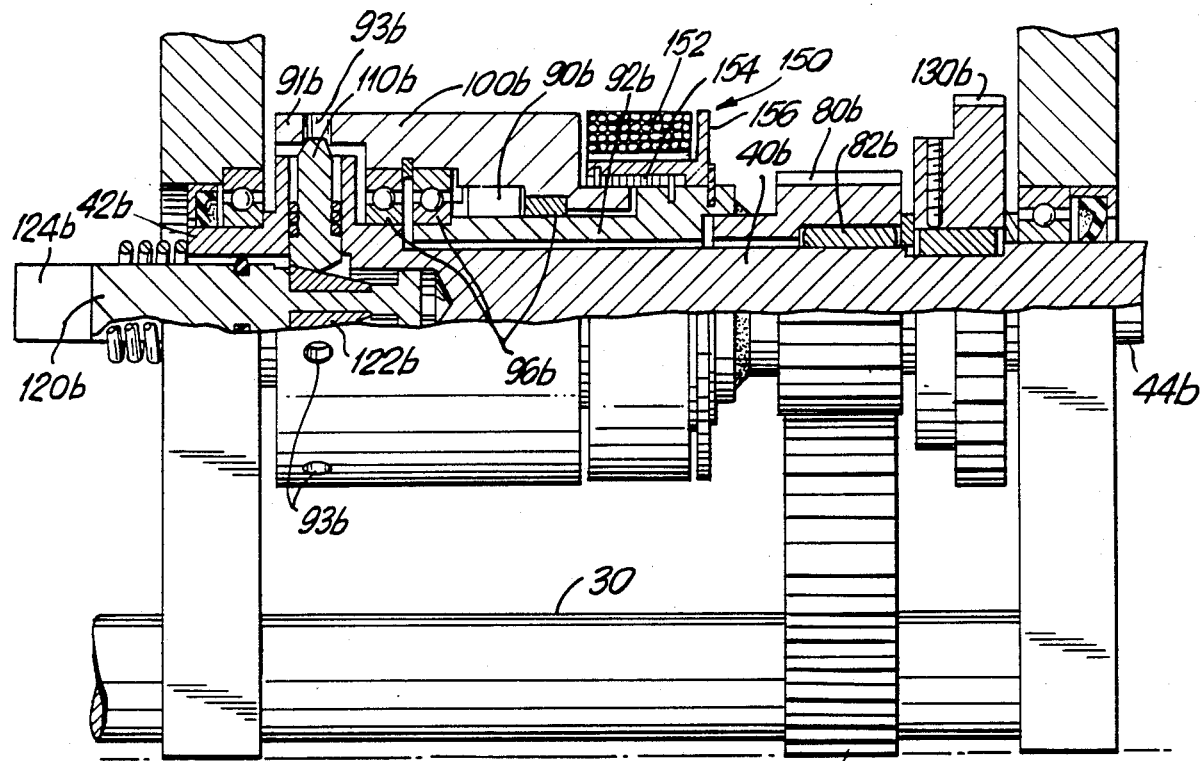
FIG. 2 is a side elevational view, partly in section, of the first parallel shaft of the dynamometer along lines 2—2 of FIG. 1.
Figure 3:
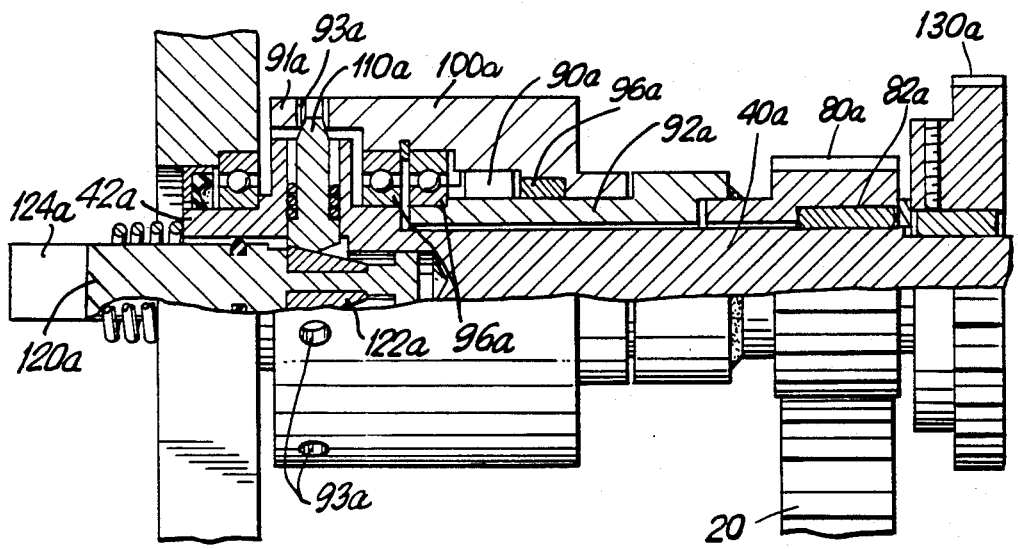
FIG. 3 is a side elevational view, partly in section, of the second parallel shaft of the dynamometer along lines 3—3 of FIG. 1.

The dynamometer 10 also has two parallel shafts 40a and 40b. FIGS. 2 and 3 are side elevational views, partly in section, of the parallel shafts 40b and 40a, respectively, along lines 2—2 and 3—3 of FIG. 1. First ends 42a and 42b of parallel shafts 40a and 40b are connected to conventional electro-mechanical actuation devices such as solenoids and springs, shown schematically as elements 124a and 124b in FIGS. 3 and 2, respectively. Other conventional electro-mechanical actuation devices may be used. A second end 44b of parallel shaft 40b is connected to a cycloidal speed reducer 50. The speed reducer 50 is connected to a DC servo motor 70 by a timing belt 60.

Two smaller spur gears 80a and 80b are supported on parallel shafts 40a and 40b by bearings 82a and 82b as shown in FIGS. 3 and 2. The bearings 82a and 82b are needle roller bearings in a preferred embodiment, but may be any other suitable component such as bushings, for supporting the spur gears 80a and 80b on the shafts 40a and 40b. Spur gears 80a and 80b may rotate independently of parallel shafts 40a and 40b. The smaller spur gears 80a and 80b are meshed with the larger spur gear 20.

Fine tooth spur gears 130a and 130b are fixed on shafts 40a and 40b by set screws or the like and gear together the parallel shafts 40a and 40b.

The smaller spur gears 80a and 80b are connected to inner races 92a and 92b of sprag clutches 90a and 90b. The outer races 100a and 100b of sprag clutches 90a and 90b are supported by bearings 96a and 96b (which are a combination of ball bearings and needle roller bearings, or any other suitable supporting components) fixed to the inner races 92a and 92b and the parallel shafts 40a and 40b.

Figure 4:
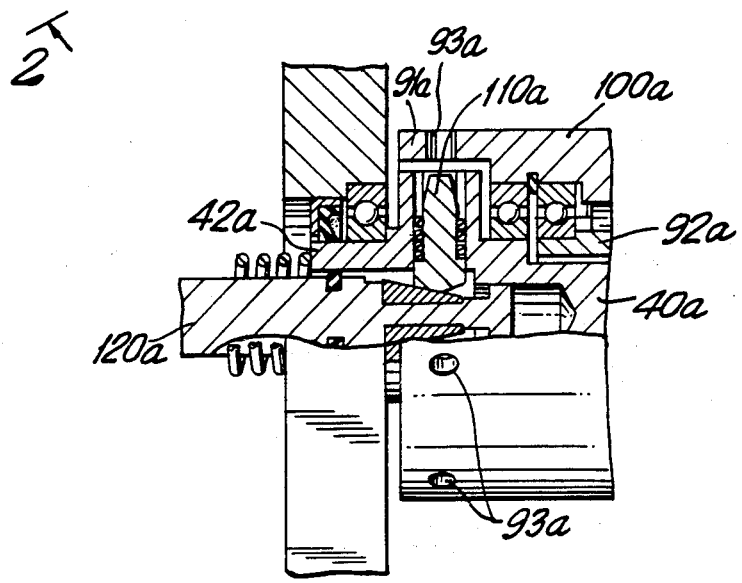
FIG. 4 is a partial side elevational view in section of either the first or second parallel shaft of the dynamometer of FIG. 1, wherein an outer race of a sprag clutch on the parallel shaft is not to the parallel shaft.

First ends of each outer race 100a and 100b form cups 91a and 91b, with a number of radial holes 93a and 93b. Pins 110a and 110b, connected to shafts 40a and 40b, respectively, engage in the radial holes 93a and 93b, thus locking the outer races 100a and 100b to the parallel shafts 40a and 40b, respectively. In the preferred embodiment there are three pins on each shaft, and six radial holes on each outer race. The pins 110a and 110b are actuated by the electro-mechanical actuation devices 124a and 124b, respectively connected to ends 42a and 42b of parallel shafts 40a and 40b. The actuation is accomplished by utilizing plungers 120a and 120b having conical portions 122a and 122b. The plungers 120a and 120b are connected to the electro-mechanical devices 124a and 124b. Actuation of the electromechanical devices 124a and 124b respectively causes the conical plungers 120a and 120b to be moved to the right (looking at the figures), resulting in the conical portions 122a and 122b pushing the pins 110a and 110b up and into engagement in the radial holes 93a and 93b, thus locking the outer races 100a and 100b to the parallel shafts 40a and 40b, respectively. It has been found that three pins equally spaced around the circumference of the shaft provide sufficient support to maintain locking. The six radial holes are also equally spaced around the outer race. Six radial holes are utilized to limit rubbing of the pins against the outer race once the pins are activated. FIGS. 2 and 3 show the pins 110b and 110a engaged in the radial holes 93b and 93a, while FIG. 4 shows, for an example, one of the pins 110a retracted from the radial holes 93a.

Also located beside outer race 100b on parallel shaft 40b is a solenoid actuated spring clutch 150 which locks together the inner race 92b and the outer race 100b of sprag clutch 90b to prevent overrunning between the inner race 92b and the outer race 100b when the spring clutch 150 is engaged. This results in the inner race 92b and the outer race 100b being locked together at all times when spring clutch 150 is energized. The spring clutch 150 is energized and the outer race 100a of the clutch 90a unlocked when it is desired to engage the user's limb in eccentric contractions in both directions of rotational movement, as described below.

Spring clutch 150 is of conventional construction and consists of a coil 152, a wrap spring 154 and a control collar 156, and is described in greater detail below with regard to the eccentric-eccentric mode of operation.

MODES OF OPERATION

Concentric-Concentric Mode

In this mode, the user's limb engages in concentric contractions in both directions of rotation of the input shaft 30. The outer races 100a and 100b are locked to the shafts 40a and 40b respectively by engaging the pins 110a and 110b in the radial holes 93a and 93b of cups 91a and 91b as described above and as shown in FIGS. 3 and 2, respectively.

Motor 70, through timing belt 60 and speed reducer 50, turns parallel shaft 40b. Since parallel shafts 40a and 40b are geared directly together by fine mesh gears 130a and 130b, shaft 40a turns in the opposite direction to shaft 40b, at the identical speed. In this mode, the outer races 100a and 100b of the clutches 90a and 90b also rotate in opposite directions relative to one another since the outer races 100a and 100b are locked to their respective parallel shafts 40a and 40b by pins 110a and 110b.

Both clutches 90a and 90b are overrunning, with their inner races 92a and 92b, which are geared to the input shaft 30, both stationary so long as the input shaft 30 is stationary. The clutches 90a and 90b are overrunning in opposite directions because their respective outer races are rotating in opposite directions to one another.

When the limb engaging means 1000 (FIGS. 5-7), such as a handle, lever arm or input arm attached to the input shaft 30, is rotated by the user, and thus accelerated in a first rotational direction, the inner races 92a and 92b both rotate in a second direction opposite to the first direction due to the action of the large spur gear 20. Since the outer races 100a and 100b are rotating in opposite directions relative to one another, one of the inner races, depending on the direction of rotation of the input shaft 30, catches up to the speed of its respective outer race. For example, assume that when the input shaft 30 is rotated in the first direction in response to force by the user's limb, inner race 92a catches up to the speed of its outer race 100a and the inner race 92b, which is rotating in the second direction, opposite to its outer race 100b, causes clutch 90b to overrun even faster.

In this example, when inner race 92a reaches the speed of outer race 100a, clutch 90a locks at a speed determined by motor 70 in combination with reducer 50. This is a well-known feature of overrunning clutches, whereby the inner race of an overrunning clutch will be locked to the outer race so long as the inner race and the outer race are rotating at the same speed in the same direction (i.e. the net speed differential is zero). Another feature of overrunning clutches is that they overrun only in one direction. If the outer race of an overrunning clutch is rotated in the direction which does not result in an overrunning condition, then the outer race and inner race are locked together, and the outer race pushes the inner race with it in that opposite direction. This feature of overrunning clutches is important in the concentric-eccentric mode, as discussed below.

In the concentric-concentric mode, the force provided by the user to the input shaft 30 back drives the system, causing the muscles of the user's limb to engage in concentric contractions in the direction of rotation of the input shaft 30. In other words, once clutch 90a locks at the set speed determined by the reducer 50 and the motor 70, no matter how much torque the user exerts, the user cannot accelerate the input shaft 30 to a higher speed, since the dynamometer 10 operates in an isokinetic fashion, as that term is defined in the Background of the Invention section above. The resistance to acceleration is provided by the motor 70 which is designed to absorb a substantial torque input without overspeeding. This results in the desired concentric contractions, as the system absorbs torque which is exerted by the user's limb in the direction of rotation of the input shaft 30.

In the above-described example, clutch 90b is overrunning, and therefore has no effect on the dynamometer 10 for this first direction of rotation of the input shaft 30.

When the user changes to the second rotational direction for the input shaft 30, inner race 92b catches up to the speed of outer race 100b, causing clutch 90b to lock. The force provided by the user back drives the system, causing the muscles of the user's limb to engage in concentric contraction in this second direction of rotation of the input shaft 30. Once clutch 90b locks at the set speed determined by the reducer 50 and the motor 70, no matter how much torque the user exerts, the user cannot accelerate the input shaft 30 to a higher speed. This results in the desired concentric contractions, as the system absorbs torque which is exerted by the user's limb in this second rotational direction of the input shaft 30. Even though input shaft 30 is turning in this second rotational direction the back driving torque applied by the use to the input shaft 30 is trying to drive the gear reducer 50 and motor 70 in the same direction of rotation as during the movement of input shaft 30 in the first rotational direction. This is due to the opposite-acting nature of gears 130a and 130b.

During the contraction in the second rotational direction of the input shaft 30, clutch 90a is overrunning, and therefore has no effect on the dynamometer 10.

The dynamometer 10 of the present invention therefore allows for concentric contractions by the user in both directions of rotation of the input shaft 30. Free-limb acceleration is possible in both direction of rotation of the input shaft 30, as the user does not encounter any resistance when accelerating to the test speed, due to the overrunning-clutch arrangement. As the user rotates the input shaft 30, and thereby the inner races of the clutches 90a and 90b, those inner races are free to rotate without resistance until one of the inner races catches up to its outer race, causing that clutch to lock.

Concentric-Eccentric Mode

The dynamometer 10 of the present invention can be easily and quickly adjusted to allow for concentric contractions in one direction of rotation of the input shaft 30 and for eccentric contractions in the other direction of rotation of the input shaft 30. For example, concentric contractions can be used for knee bending (flexion) and eccentric contractions can be used for the motion involved when the user attempts to resist extending the knee (extension). Knee flexion and extension are shown generally in FIG. 5, with extension being in the direction of arrow (a) and flexion being in the direction of arrow (b), with the limb engaging means 1000 connected to the input shaft 30 in the dynamometer 10. FIG. 6 shows elbow flexion (arrow (a)) and elbow extension (arrow (b)). Similarly, FIG. 7 shows shoulder flexion (arrow (a)) and shoulder extension (arrow (b)).

In this concentric-eccentric mode, one of the clutches 90a or 90b is completely disengaged from the system. For sake of illustration, clutch 90a is disengaged. The disengagement is accomplished by deactivating the electro-mechanical device 124a connected to the plunger 120a. This causes plunger 120a to be withdrawn and results in the pins 110a not being engaged in the radial holes 93a in cup 91a, as shown in FIG. 4. It is understood that pins 110b may also be disengaged from the radial holes 93b in cup 91b in an identical manner to that shown in FIG. 4.

With the input shaft 30 stationary, clutch 90b, whose outer race 100b is engaged by pins 110b, is overrunning, and, because pins 110a are not engaged in the radial holes 93a in cup 91a, the clutch 90a is completely disengaged.

The user's limb then rotates the input shaft 30 in the first rotational direction which causes the inner race 92b to catch up to the outer race 100b of clutch 90b. Once the speed of inner race 92b equals the speed of outer race 100b, clutch 90b locks as described above with relation to the concentric-concentric mode, and the dynamometer 10 absorbs torque in this first rotational direction of rotation of the input shaft 30 by the user, resulting in concentric contractions. Because of the overrunning-clutch arrangement, free-limb acceleration is possible during the concentric contraction motion for the concentric-eccentric mode.

Figure 8:
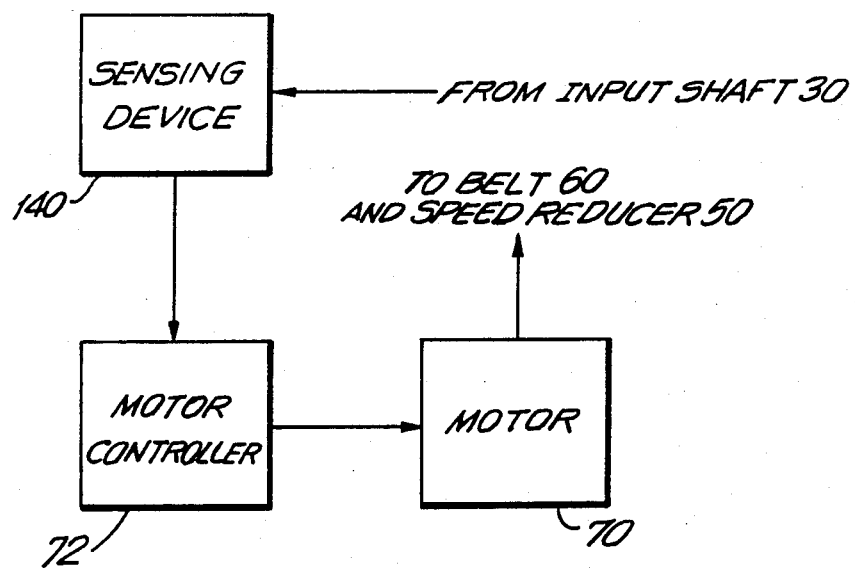
FIG. 8 is a block diagram showing the basic components needed for reversing the direction of the motor.

After the user completes the concentric contraction in the first rotational direction, the direction of motor 70 is reversed. The manner in which this is accomplished is shown schematically in FIG. 8.

A sensing device 140, for example an optical encoder or a potentiometer, attached to the input shaft 30, provides a motor controller 72 with information regarding the rotational position of the input shaft 30 during the concentric contraction. The motor controller 72, which in the preferred embodiment contains a microprocessor, may be programmed to change the motor speed to zero when a certain rotational position of the input shaft 30 is reached. The set position can be varied, depending upon the range capabilities of the user. When the motor controller 72 reduces the speed of the motor 70 to zero, this prevents the user from rotating the input shaft 30 any further. After the motor 70 reaches zero speed, it reverses direction at the instruction of the motor controller 72 and increases to the set speed, but in the reverse direction. When the motor 70 reverses direction, the outer race 100b turns in the opposite direction. Clutch 90b is no longer overrunning. Since the nature of overrunning clutches is that they only overrun in one direction, reversing the motor 70 causes the outer race 100b to push the inner race 92b in the same direction of outer race 100b, i.e., inner race 92b becomes locked to outer race 100b. Since inner race 90b is connected to the input shaft 30, reversing the motor 70 causes the input shaft 30 to actively move the limb engaging means and thereby the user's limb.

This causes the user's limb, which is secured to the limb engaging means 1000, to be forced back in the direction opposite that of the concentric contraction. The forcing back of the user's limb while the dynamometer 10 absorbs the torque applied by the user's limb constitutes the eccentric contraction. In other words, as the user tries to resist the return motion as driven by the motor 70, an eccentric contraction takes place.

To reverse the pattern of eccentric-concentric contractions in this mode, clutch 90a is engaged by reengaging the pins 110a into the radial holes 93a of cup 91a and clutch 90b is disengaged by withdrawing pins 110b from the radial holes 93b in cup 91b.

At all times during eccentric contractions in the concentric-eccentric mode of operation, the user can pull away or move away from the load as a safety feature. In other words, the user can avoid being pushed by the handle or lever arm by quickly rotating the handle or lever arm away from the direction of the force of the input shaft 30. For example, if clutch 90b is locked during the eccentric contraction, the user can unlock the clutch 90b by quickly rotating the input shaft 30 faster in the direction of motion of the input shaft 30. This will cause the inner race 92b to pull away from the outer race 100b. The relative motion between the inner race 92b and the outer race 100b results in an overrun condition, unlocking the clutch 90b. The clutch 90b will relock, however, when the outer race 100b catches up to the inner race 92b.

If one of the clutches is disengaged, e.g. pins 110a are withdrawn from radial holes 93a, and no provision is made for reversing the direction of the motor 70, then the dynamometer 10 will allow for concentric muscular contractions in one direction of rotation of the input shaft 30. In the opposite direction of rotation of the input shaft 30, the user will not encounter any resistance other than the weight of the limb engaging means 1000 and the input shaft 30.

Eccentric-Eccentric Mode

In this mode clutch 90a is disengaged in the manner previously described, i.e., pins 110a are withdrawn from engagement in radial holes 93a. Clutch 90b is engaged by the electro-mechanical actuation device 124b on end 42b of shaft 40b, pushing plunger 120b and causing conical section 122b to push pins 110b up into the radial holes 93b of cup 91b. This results in the outer race 100b being locked to the parallel shaft 40b.

Figure 2A:
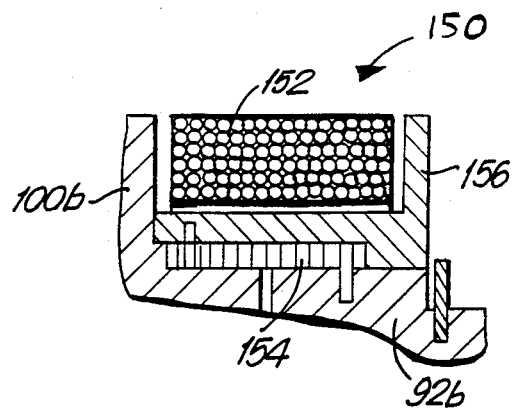
FIG. 2A is a partial side elevational view in section showing a spring clutch of FIG. 2 energized to lock together a first outer race and a second outer race of a first overrunning clutch on the first parallel shaft.

Spring clutch 150 is also engaged. The spring clutch 150 is energized and therefore engaged by means of a conventional solenoid. As previously described spring clutch 150 is of conventional construction and consists of a coil 152, a wrap spring 154 and a control collar 156. Engagement of the spring clutch 150 is shown in FIG. 2A.

The wrap spring 154 is coupled to the control collar 156 at one end and the inner race 92b at the other end.

When the coil 152 is energized, the control collar 156 is drawn in until it rubs against the outer race 100b. When sprag clutch 90b overruns, inner race 92b is stationary while outer race 100b rotates, dragging control collar 156 along with it, winding the wrap spring 154 tightly around the inner race 92b and the outer race 100b, and thereby locking the inner race and the outer race together.

With spring clutch 150 energized, outer race 100b is locked to inner race 92b. Therefore, inner race 92b, which is connected to the input shaft 30, is also connected to parallel shaft 40b. It is readily seen that since motor 70 drives parallel shaft 40b, input shaft 30 is also driven by motor 70 when spring clutch 150 is energized. When the motor 70 changes direction at the end of the eccentric contraction in a first direction in response to signals from the sensing device 140 and the motor controller 72, shaft 30 is then driven in the second direction. Thus, in this eccentric-eccentric mode, the user's limb is driven by input shaft 30 in both directions of rotation of input shaft 30, resulting in eccentric contractions in both directions.

The dynamometer 10 does not jam because clutch 90a is disengaged in this mode. Once pins 110a are disengaged from cup 91a, outer race 100a is free to rotate or not rotate and has no effect on shaft 40a, which is the link through the gear train to motor 70.

The dynamometer of the present invention allows for concentric and eccentric contractions in as safe a manner as possible and also allows for free-limb acceleration up to the test speed when the user is engaged in concentric contractions.

The basic design of the dynamometer 10 has many inherent desirable attributes. For example, the clutch disconnect mechanism isolates the user from the power source 70, even when the spring clutch 150 is energized thereby locking outer race 100b and inner race 92b together. The clutches 90a and 90b, when locked, will always release under the highest torques because the angles on the conical sections 122a and 122b and the pins 110a and 110b make the release self-actuating.

Also, the electro-mechanical devices 124a and 124b which engage the pins 110a and 110b into radial holes 93a and 93b require power to stay locked. Therefore, a power loss assures that the pins 110a and 110b will be withdrawn and the clutches 90a and 90b disengaged, releasing the user from the system. In the concentric-concentric mode of operation, when the user stops rotation of the input shaft 30, the user encounters no resistance even though the motor 70 is still running. This is due to the overrunning clutch arrangement.

In the concentric-eccentric mode of operation, when the dynamometer is operating to provide an eccentric contraction, the user can pull away from the applied load simply by moving the limb in the same rotational direction as the movement of the input shaft 30, but at a faster rate than the test speed. In the concentric-eccentric mode, when the dynamometer is operating to provide an eccentric contraction, the instant the speed of the input shaft 30, as driven by the user, exceeds the speed the shaft 30 is driven by the motor 70, reducer 50 and the gear train, the engaged clutch (either clutch 90a or clutch 90b) will in effect overrun due to the relative motion between the inner race and the outer race, preventing any torque from the motor 70 from being applied to the user's limb.

In the eccentric-eccentric mode of operation, if the torque exerted by the user falls below or exceeds predetermined levels, a clutch disconnect system can be disengaged, causing the outer race 110b and the inner race 92b to become unlocked, essentially disconnecting the user from the motor 70. Such a clutch disconnect system includes means for measuring torque exerted by the user, such as strain gauges. The actuation devices can be deactivated if the torque measured is below or above certain threshholds.

In all modes, the motor 70 may be shut down by the user as another safety feature. The safety features listed above, which do not depend on motor shutdown, greatly enhance the safety aspects of the dynamometer of the present invention. It is believed that the dynamometer of the present invention provides the greatest safety available for dynamometers capable of testing both concentric and eccentric muscular contractions.

Various modes of operation for the dynamometer 10 are possible. The above description relates to a constant speed mode for both concentric and eccentric contractions. Isotonic (constant torque), programmed velocity, programmed force and multi-angle isometric modes are also possible with the dynamometer 10 by changing the servo motor control for motor 70.

It is understood that the present invention is not limited to the embodiment described above but is defined by the following claims.

I claim:

1. An improved human performance dynamometer for testing muscle contractions of a user exerted against a limb engaging means, the dynamometer comprising:
    a first parallel shaft;
    a second parallel shaft;
    a rotative power means rotating in a first rotational direction at a first rotational speed, said rotative power means connected either to the first parallel shaft or the second parallel shaft;
    first gearing means for gearing together the first parallel shaft and the second parallel shaft;
    a first overrunning clutch supported on the first parallel shaft, said first overrunning clutch having a first outer race and a first inner race;
    a second overrunning clutch supported on the second parallel, a shaft, said second overrunning clutch having a second outer race and a second inner race;
    an input shaft connected to the limb engaging means;
    second gearing means for gearing the input shaft to the first inner race and the second inner race, whereby when the user exerts a force in a second rotational direction on the limb engaging means, the input shaft rotates in the second rotational direction, and the first inner race and the second inner race both rotate in the first rotational direction and whereby when the user exerts a force in the first rotational direction on the limb engaging means, the input shaft first rotates in the first rotational direction, and the first inner race and the second inner race both rotate in the second rotational direction;
    first engagement means for locking the first outer race to the first parallel shaft and for unlocking the first outer race from the first parallel shaft; and
    second engagement means for locking the second outer race to the second parallel shaft and for unlocking the second outer race from the second parallel shaft, whereby when the first outer race is locked to the first parallel shaft and the second outer race is locked to the first parallel shaft, rotation of the limb engaging means by the user in either the first rotational direction or the second rotational direction at a second rotational speed which is proportional to the first rotational speed results in concentric muscular contractions with free-limb acceleration.

2. The dynamometer of claim 1 also comprising means for reversing the direction of rotation of the rotative power means thereby allowing for concentric muscular contractions with free-limb acceleration in one direction of rotation of the input shaft and eccentric muscular contractions in the opposite direction of rotation of the input shaft when either the first outer race or the second outer race is unlocked from its respective parallel shaft.

3. The dynamometer of claim 2 also comprising third engagement means for locking the first outer race to the first inner race thereby allowing for eccentric muscular contractions in one direction of rotation of the input shaft and eccentric muscular contractions in the opposite direction of rotation of the input shaft when either the first outer race or the second outer race is unlocked from its respective parallel shaft.

4. The dynamometer of claim 3 wherein the third engagement means comprises a solenoid spring clutch on the first parallel shaft, said spring clutch comprising a coil, a control collar and a wrap spring, said wrap spring connected at a first end to the control collar and connected at a second end to the first inner race, whereby when the coil is energized, the control collar is drawn against the first outer race and whereby when the first clutch overruns, the wrap spring is wound tightly around the first inner race and the first outer race, thereby locking the first inner race and the first outer race together.

5. The dynamometer of claim 2 wherein the rotative power means comprises a speed reducer connected to either the first parallel shaft or the second parallel shaft and a motor connected to the speed reducer.

6. The dynamometer of claim 5 wherein the reversing means comprises a position sensor connected to the input shaft for measuring the rotational position of the input shaft and a motor controller connected to the position sensor and to the motor, whereby once the input shaft reaches a desired rotational position, the motor controller instructs the motor to reduce its speed to zero and then to the first rotational speed in the second rotational direction.

7. The dynamometer of claim 1 wherein the first gearing means comprises a first spur gear fixed to the first parallel shaft and a second spur gear fixed to the second parallel shaft wherein the first spur gear and the second spur gear are meshed with one another.

8. The dynamometer of claim 1 wherein the second gearing means comprises a third spur gear fixed to the input shaft, a fourth spur gear connected to the first inner race and supported on the first parallel shaft, whereby the fourth spur gear and the first parallel shaft can rotate independently of one another, and a fifth spur gear connected to the second inner race and supported on the second parallel shaft whereby the fifth spur gear and the second parallel shaft can rotate independently of one another, wherein the fourth and fifth spur gears are meshed with the third spur gear.

9. The dynamometer of claim 1 wherein the first engagement means comprises a first cup with a plurality of first radial holes located in the first outer race, a plurality of first pins movably connected to the first parallel shaft and first moving means for moving the first pins into and out of engagement in the first radial holes of the first cup.

10. The dynamometer of claim 9 wherein the first moving means comprises a first plunger connected at a first end to a first actuation device and having a first conical portion at a second end, whereby actuation of the first actuation device causes the first conical portion to push the first pins up into engagement with the first radial holes in the first cup.

11. The dynamometer of claim 1 wherein the second engagement means comprises a second cup with a plurality of second radial holes located in the second outer race, a plurality of second pins movably connected to the second parallel and second moving means for moving the second pins into a engagement in the second radial holes of the second cup.

12. The dynamometer of claim 11 wherein the second moving means comprises a second plunger connected at a first end to a second actuation device and having a second conical portion at a second end, whereby actuation of the second actuation device causes the second conical portion to push the second pins up into engagement with the second radial holes in the second cup.

* * * * *